United States Patent [19]

Ramirez et al.

[11] Patent Number: 5,149,786
[45] Date of Patent: Sep. 22, 1992

[54] DOPAMINE RELEASING PROTEIN AND ANTIBODY

[75] Inventors: Victor D. Ramirez, Champaign, Ill.; Frank Marcus, Danville, Calif.

[73] Assignee: Chiron Corporation, Emeryville, Calif.

[21] Appl. No.: 420,830

[22] Filed: Oct. 12, 1989

[51] Int. Cl.⁵ ............ C07K 15/00; A61K 37/43; A61K 39/00

[52] U.S. Cl. ................... 530/350; 530/395; 514/8; 424/85.8

[58] Field of Search ............ 530/350, 395; 514/8; 424/85.8

[56] References Cited

FOREIGN PATENT DOCUMENTS 324037 7/1989 European Pat. Off. .

OTHER PUBLICATIONS

Milstein, "Overview: Monoclonal Antibodies" Handbook of Experimental Immunology 4th ed. (Alden Press: Oxford) 1986.
R. J. Wurtman et al., *Pharmacol Rev* (1972) 24:411–26.
A. S. Hartree et al., *Meth Enzymol* (1979) 37B:380–89.
A. Bjorklund et al., *Brain Res* (1979) 177:555–60.
M. J. Perlow et al., *Science* (1979) 204:643–47.
M. J. Perlow et al., *Proc. Nat Acad Sci USA* (1980) 77:5278–81.
W. J. Freed et al., *Nature* (1981) 292:351–52.
Chen and Ramirez, *Endocrinol* (1982) 111:1740–42.
P. A. Broderick et al., *Brain Res* (1983) 269:378–81.
M.-F. Chesselet et al., *J Neurosci* (1983) 3:232–36.
W. J. Freed et al., *Brain Res* (1983) 269:184–89.
M. Herrera-Marchitz et al., *Brian Res* (1984) 297:53–61.
E. O. Backlund et al., *J Neurosurg* (1985) 62:169–73.
T. F. Freund et al., *J. Neurosci* (1985) 5:603–16.
I. Stromberg et al., *Exp Brain Res* (1985) 60:335–49.
I. Stromberg et al., *Neurosci* (1985) 14:981–90.
H. Thoenen et al., *Science* (1985) 229:238–42.
Chang and Ramirez, *Brain Res* (1986) 368:134–40.
F. Petit et al., *Neuropharmacol* (1986) 25:1015–21.
H. Winkler et al., *Neurosci* (1986) 18:261–90.
T. Zetterstrom et al., *Brain Res* (1986) 362:344–49.
M. C. Bohn et al., *Science* (1987) 237:913–16.

*Primary Examiner*—David L. Lacey
*Assistant Examiner*—Shelly J. Guest
*Attorney, Agent, or Firm*—Grant D. Green

[57] ABSTRACT

Dopamine releasing protein (DARP) is a protein which stimulates release of dopamine from dopaminergic neurons, and is effective at extremely low concentrations. DARP is useful for stimulating vertebrate nervous systems, and potentially for treatment of Parkinson's disease. Antibodies to DARP are useful for inhibiting dopamine release, and for quantifying the concentration of DARP in samples.

6 Claims, 4 Drawing Sheets

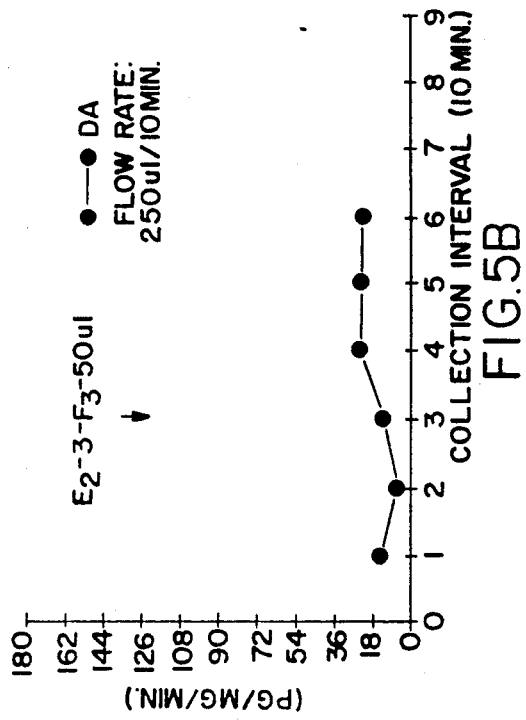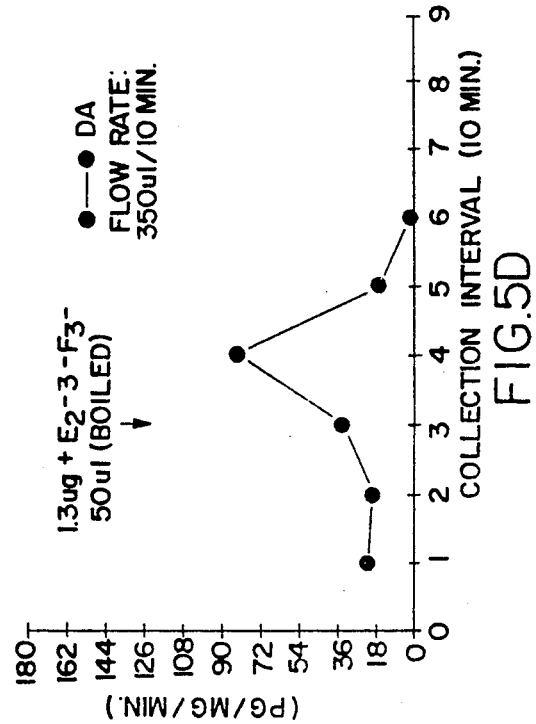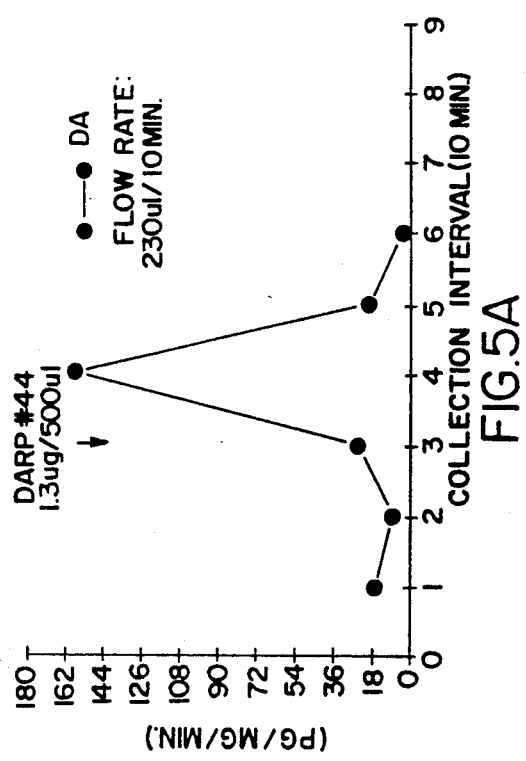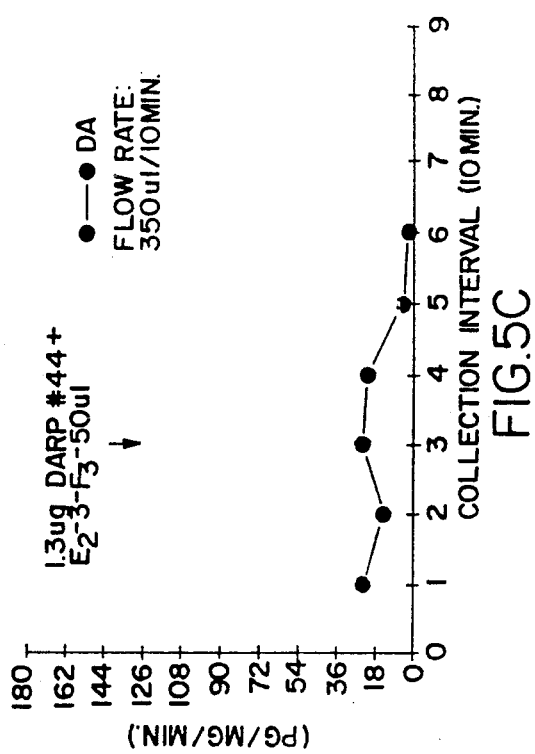

DOPAMINE RELEASING PROTEIN AND ANTIBODY

This invention was made with U.S. Government support under Grant No. 3R01 HD14625-09S1, awarded the National Institutes of Health. The U.S. Government has certain rights in this invention.

TECHNICAL FIELD

This invention relates to the fields of molecular biology, neurochemistry, and neurophysiology. More particularly, this invention relates to a dopamine-releasing protein (DARP) derived from mammalian adrenal glands, which stimulates release of dopamine from dopaminergic neurons, and to antibodies capable of neutralizing DARP activity.

BACKGROUND OF THE INVENTION

Parkinson's disease was first described in 1817, as a neurological disorder characterized by tremor, muscular rigidity, and loss of postural reflexes. It typically presents in middle age, and is a leading cause of neurological disability in individuals 60 and older. Current estimates are that 100–150 of every 100,000 people are afflicted with Parkinson's disease.

Early signs of the disease typically begin with relative immobility of facial expression, infrequent blinking, fixed trunk postures, and difficulty in sitting or rising. These signs are generally followed by symptoms of tremor, slowness and fatigue, loss of dexterity, disturbances in gait, psychological depression, and others. Later symptoms include muscular rigidity and difficulty in performing volitional motor activities. The patient may lose many reflex motions, such as eye blinking, automatic shifting of weight when standing or sitting, arm swinging while walking, which must be performed consciously. The course of Parkinson's disease is progressive, and causes severe disability or death in 25% of patients within 5 years of onset, in 65% of patients within 10 years, and in 80% of patients within 15 years.

Parkinson's disease is now associated with the gradual destruction of catecholamine neurons in the brain, particularly in the substantia nigra, locus ceruleus, and brain-stem nuclei. Dopamine concentration in the caudate nucleus, putamen, and pallidum is depleted, and is correlated with the degree of cell loss in the substantia nigra.

Current therapy is based on administration of L-DOPA, which is metabolized to dopamine in vivo. L-DOPA is often administered in combination with a peripheral decarboxylase inhibitor (e.g., carbidopa), which inhibits metabolism of dopamine, and thus reduces the amount of L-DOPA required. Others have administered monoamine oxidase (MAO) inhibitors such as deprenyl, which inhibits metabolism of dopamine by MAO, allowing the accumulation of dopamine and prolonging its action. However, L-DOPA treatment also presents a host of side effects, including involuntary movements, confusional states, and toxic psychosis. Tolerance for the drug typically develops over time, such that the dosage administered is gradually increased until contraindicated by side effects The disease continues to progress.

Lately, a great deal of interest has arisen in the possible use of tissue transplant as a means to ameliorate the progression of the disease. See for example M. Herrera-Marschitz et al, *Brain Res* (1984) 297:53–61; E-O. Backlund et al, *J Neurosurg* (1985) 62:169–73; I. Stromberg et al, *Exp Brain Res* (1985) 60:335–49; and I. Madrazo et al, *New Eng J Med* (1987) 316:831–84. Although initial results with adrenal tissue and later with substantia nigra are encouraging, the mechanism and final outcome of this approach is unknown.

The ultimate cause of Parkinson's disease is still unknown. Infectious and environmental factors have been postulated, but no infectious agents have been isolated or environmental factors linked to the disease. There is no known hereditary predisposition. However, it is possible that the selective death of dopaminergic neurons in localized areas of the brain is due to the abnormally low concentration and/or synthesis of dopamine. This in turn may be caused by the absence or depletion of endogenous releasing factors, which may be responsible for synthesis and/or release of threshold concentrations of dopamine. Our discovery tends to support such a hypothesis.

DISCLOSURE OF THE INVENTION

We have now discovered a novel protein, dopamine releasing protein (DARP), which is present in mammalian adrenal glands and brain tissue. DARP potently stimulates the release of the neurotransmitter dopamine (DA) from dopaminergic neurons, and is believed capable of stabilizing and/or ameliorating the effects of Parkinson's disease. We have also invented a method for purifying DARP from tissue extracts, which will enable identification of the molecular structure and production of DARP in sufficient quantities for animal models of Parkinson's disease and clinical trials.

We have also invented antibodies specific for DARP. Some of the MAbs are capable of neutralizing the effect of DARP. We submit that these MAbs may be used therapeutically to treat dopaminergic hyperactivity, notably in certain cases of schizophrenia. The antibodies of the invention are also useful for quantifying DARP by immunoassay.

BRIEF DESCRIPTION OF THE DRAWINGS

FIG. 5 shows the results of the antibody activity experiments performed in Example 4(B) FIG. 5A shows the dopamine release obtained by superfusion with DARP. FIG. 5B shows that DARP activity is suppressed by incubation with anti-DARP MAbs. FIG. 5C shows that administration of anti-DARP MAbs alone has no effect on the baseline dopamine release. FIG. 5D shows that boiling the anti-DARP MAbs renders them unable to suppress DARP activity completely.

MODES OF CARRYING OUT THE INVENTION

A. Definitions

Figures 1A, 1B:
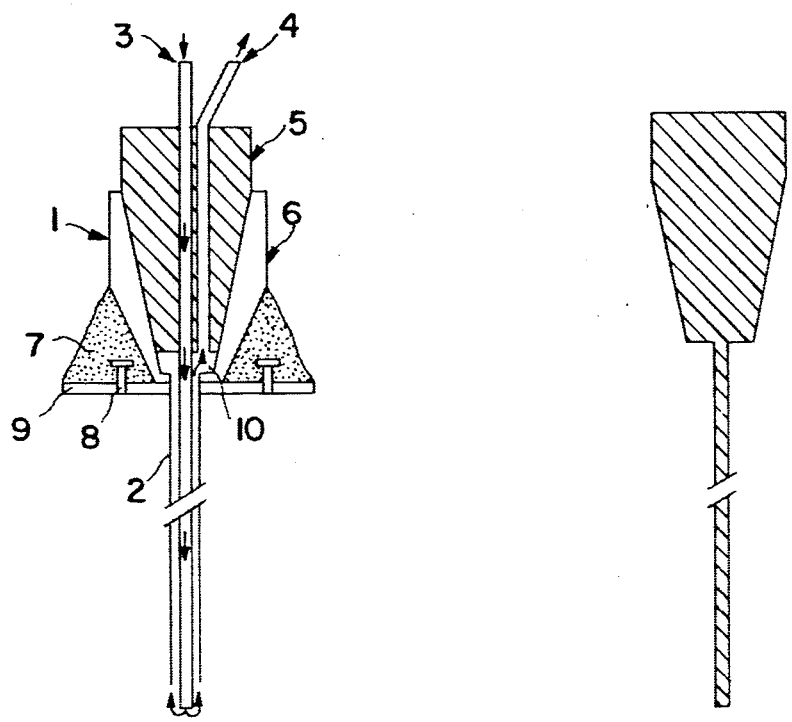
FIG. 1A is a cross-sectional illustration of a push-pull cannula useful for in vivo perfusion experiments, as described below.
FIG. 1B depicts in cross-section a stylette useful for preparing the site for insertion of the cannula.

The terms "dopamine releasing protein" and "DARP" refer to a novel, protease-sensitive factor which in a dose-dependent manner selectively stimulates the release of dopamine from striatal tissue superfused in vitro. DARP may be extracted from adrenal glands, neocortex, corpus striatum, cerebellum, and possibly from other tissues. It is apparently absent from liver and spleen tissues. DARP is an extremely potent dopamine releaser, and induces amphetamine-like behavior when administered to the caudate nucleus in laboratory animals at low ($\leq 10^{-8}$M) concentrations. DARP is partially inactivated by trypsin and completely inactivated by the nonspecific protease pronase E (Chang and Ramirez, *Brain Res* (1988) 463:385).

The term "antibody derivative" refers to Fab and F(ab')$_2$ fragments, chimeric antibodies, and the like. "Antibody derivative" includes proteins derived from antibodies or modified forms.

The term "detectable label" refers to a molecule or atom which provides a signal which can be detected and quantified. Suitable labels include enzymes capable of catalyzing reactions which form chromogenic, fluorogenic, and/or luminescent products, fluorophores, chromophores, radioactive atoms (particularly $^{32}$P and $^{125}$I), electron-dense reagents, and ligands having specific binding partners. Presently preferred labels are horseradish peroxidase and fluorescein.

The term "treatment" as used herein means cure of the disease or disorder, the complete or partial alleviation of symptoms, prevention of further disease progression, or inhibition and slowing of further progression of the disease.

B. General Method

Extraction

DARP may be extracted from mammalian tissues or may be expressed by recombinant methods. It is presently preferred to extract DARP from adrenal gland tissue, neocortex, corpus striatum, or cerebellum, especially from adrenal tissue. Fresh tissues (e.g., bovine or porcine adrenal glands) are chilled and minced, and the minced pieces sonicated in a solution of 40% EtOH/6% ammonium acetate, pH 5.1. Following centrifugation at 5000 g for 30 min, the EtOH concentration of the supernatant is brought up to 80%. After storage at $-20°$ C. overnight, the precipitate is collected by centrifugation at 5000 g for 30 min. The 80% EtOH precipitate is then dissolved, dialyzed against a modified Krebs-Ringer phosphate buffer (KRP) and used for the superfusion experiment (Chang and Ramirez, *Brain Res* (1986) 368:134). If desired, commercially available tissue preparations (for example, bovine adrenal cortex acetone powder, available from Sigma Chemical Co., St. Louis, Mo.) can be used for the purification of DARP. The purification method (described in detail in Example 1) consists of extraction, ethanol precipitation, Sephadex® G-100 gel filtration, zinc chloride fractionation, and DEAE-Sephadex® G-25 ion exchange chromatography.

Expression

The purified DARP may be microsequenced to determine enough of the amino acid sequence to allow construction of a DNA probe. The probe may be used to identify DARP coding sequences in a genomic library, or in a cDNA library derived from brain or adrenal gland tissue. The complete protein sequence may be determined using standard chromosome walk techniques. Alternatively, the DARP coding sequence may be identified in a cDNA library by cloning into lambda gt11, expressing the resulting clones, and screening for expression of DARP using an anti-DARP MAb, such as E$_2$-3-F$_3$, described herein.

DARP may be expressed recombinantly in vitro or in vivo, in either prokaryotic or eukaryotic systems. Prokaryotes are most frequently represented by various strains of *E. coli*. However, other microbial strains may also be used, such as bacilli (for example *Bacillus subtilis*), various species of Pseudomonas, and other bacterial strains. In such prokaryotic systems, plasmid vectors which contain replication sites and control sequences derived from a species compatible with the host are used. For example, *E. coli* is typically transformed using derivatives of pBR322, a plasmid derived from an *E. coli* species by Bolivar et al, *Gene* (1977) 2:95. Commonly used prokaryotic control sequences, which are defined herein to include promoters for transcription initiation, optionally with an operator, along with ribosome binding site sequences, include such commonly used promoters as the beta-lactamase (penicillinase and lactose (lac) promoter systems (Chang et al, *Nature* (1977) 198:1056) and the tryptophan (trp) promoter system (Goeddel et al, *Nuc Acids Res* (1980) 8:4057) and the lambda-derived P$_L$ promoter and N-gene ribosome binding site (Shimatake et al, *Nature* (1981) 292:128). However, any available promoter system compatible with prokaryotes can be used.

The expression systems useful in eukaryotic systems of the invention comprise promoters derived from appropriate eukaryotic genes. A class of promoters useful in yeast, for example, include promoters for synthesis of glycolytic enzymes, including those for 3-phosphoglycerate kinase (Hitzeman et al, *J Biol Chem* (1980) 255:2073). Other promoters include those from the enolase gene (M. J. Holland et al, *J Biol Chem* (1981) 256:1385) or the Leu2 gene obtained from YEp13 (J. Broach et al, *Gene* (1978) 8:121).

Suitable mammalian promoters include the early and late promoters from SV40 (Fiers et al, *Nature* (1978) 273:113) or other viral promoters such as those derived from polyoma, adenovirus II, bovine papilloma virus, or avian sarcoma viruses. Suitable viral and mammalian enhancers are cited above. In the event plant cells are used as an expression system, the nopaline synthesis promoter is appropriate (A. Depicker et al, *J Mol Appl Gen* (1982) 1:561). Expression in insect cell culture may conveniently be achieved using a baculovirus vector.

Transformation

Depending on the host cell used, transformation is done using standard techniques appropriate to such cells. The calcium treatment employing calcium chloride, as described by S. N. Cohen, *Proc Nat Acad Sci*

USA (1972) 69:2110, or the RbCl method described in T. Maniatis et al, *Molecular Cloning: A Laboratory Manual* (1982) Cold Spring Harbor Press, p. 254, is used for prokaryotes or other cells which contain substantial cell well barriers. Infection with *Agrobacterium tumefaciens* (C. H. Shaw et al, Gene (1983) 23:315) is used for certain plant cells. For mammalian cells without cell walls, the calcium phosphate precipitation method of Graham and van der Eb, *Virology* (1978) 52:546 is preferred. Transformations into yeast are carried out according to the method of P. Van Solingen et al, *J Bacter* (1977) 130:946 and C. L. Hsiao et al, *Proc Nat Acad Sci USA* (1979) 76:3829. Alternatively, one may use a liposomal transfection system. For example, one may use a synthetic lipid such as N-[1-(2,3-dioleyloxy)propyl]-N,N,N-trimethylammonium chloride, commercially available under the name Lipofectin ® (BRL, Gaithersburg, Md.), as described by P. L. Felgner et al, *Proc Nat Acad Sci USA* (1987) 84:7413.

Probing cDNA or Genomic Libraries cDNA or genomic libraries may be screened by colony hybridization. Each microtiter plate is replicated onto duplicate nitrocellulose filter papers (e.g., S & S type BA-85) and colonies are allowed to grow at 37° C. for 14–16 hr on L agar containing 50 ug/mL Amp. The colonies are lysed and DNA fixed to the filter by sequential treatment for 5 min with 500 mM NaOH, 1.5M NaCl, and are washed twice for 5 min each time with 5X standard saline citrate (SSC). Filters are air dried and baked at 80° C. for 2 hr. The duplicate filters are prehybridized at 42° C. for 6–8 hr with 10 mL per filter of DNA hybridization buffer (5× SSC, pH 7.0, 5× Denhardt's solution (polyvinylpyrrolidone, plus Ficoll and bovine serum albumin; 1× =0.02% of each), 50 mM sodium phosphate buffer at pH 7.0, 0.2% SDS, 20 ug/mL poly-U, and 50 ug/mL denatured salmon sperm DNA).

The samples are hybridized with kinased probe under conditions which depend on the stringency desired. Typical moderately stringent conditions employ a temperature of 42° C. for 24–36 hr with 1–5 mL/filter of DNA hybridization buffer containing probe. For higher stringencies, high temperatures and shorter times are employed. The filters are washed four times for 30 min each time at 37° C. with 2× SSC, 0.2% SDS and 50 mM sodium phosphate buffer at pH 7, then washed twice with 2× SSC and 0.2% SDS, air dried, and are autoradiographed at −70° C. for 2 to 3 days.

Vector Construction

Construction of suitable vectors containing the desired coding and control sequences employs standard ligation and restriction techniques which are well understood in the art. Isolated plasmids, DNA sequences, or synthesized oligonucleotides are cleaved, tailored and religated in the form desired.

Site specific DNA cleavage is performed by treatment with a suitable restriction enzyme (or enzymes) under conditions which are generally understood in the art, generally following the manufacturer's directions. See, e.g., New England Biolabs, Product Catalog. In general, about 1 ug of plasmid or DNA sequence is cleaved by one unit of enzyme in about 20 uL of buffer solution; in the examples herein, typically, an excess of restriction enzyme is used to insure complete digestion of the DNA substrate. Incubation times of about 1 hr to 2 hr at about 37° C. are workable, although variations can be tolerated. After each incubation, protein is removed by extraction with phenol/chloroform, and may be followed by diethyl ether extraction, and the nucleic acid recovered from aqueous fractions by ethanol precipitation followed by separation over a Sephadex ® G-50 spin column. If desired, size separation of the cleaved fragments may be performed by polyacrylamide gel or agarose gel electrophoresis using standard techniques. A general description of size separations is found in *Meth Enzymol* (1980) 65:499–560.

Restriction cleaved fragments may be blunt ended by treating with the large fragment of *E. coli* DNA polymerase I (Klenow) in the presence of the four deoxyribonucleotide triphosphates (dNTPs) using incubation times of about 15 to 25 min at 20° to 25° C. in 50 mM Tris, pH 7.6, 50 mM NaCl, 6 mM $MgCl_2$, 6 mM DTT and 5–10 uM dNTPs. The Klenow fragment fills in at 5' sticky ends but chews back protruding 3' single strands, even though the four dNTPs are present. If desired, selective repair can be performed by supplying only 1–3 of the dNTPs, within the limitations dictated by the nature of the sticky ends. After treatment with Klenow fragment, the mixture is extracted with phenol/chloroform and ethanol precipitated, followed by running over a Sephadex ® G-50 spin column. Treatment under appropriate conditions with S1 nuclease results in hydrolysis of any single-stranded portion.

Synthetic oligonucleotides are prepared by the triester method of Matteucci et al (*J Am Chem Soc* (1981) 103:3185) or using commercially available automated oligonucleotide synthesizers. Kinasing of single strands prior to annealing or for labeling is achieved using an excess, e.g., approximately 10 units of polynucleotide kinase to 0.1 nmole substrate in the presence of 50 mM Tris, pH 7.6, 10 mM $MgCl_2$, 5 mM dithiothreitol, 1–2 mM ATP, 1.7 pmoles $^{32}P$-ATP (2.9 mCi/mmole), 0.1 mM spermidine, and 0.1 mM EDTA.

Ligations are performed in 15–30 uL volumes under the following standard conditions and temperatures: 20 mM Tris-HCl, pH 7.5, 10 mM $MgCl_2$, 10 mM DTT, 33 ug/mL BSA, 10 mM-50 mM NaCl, and either 40 uM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 ug/mL total DNA concentrations (5–100 nM total end concentration). Intermolecular blunt end ligations (usually employing a 10–30 fold molar excess of linkers) are performed at 1 uM total ends concentration.

In vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 mM Tris, in the presence of $Na^+$ and $Mg^{2+}$ using about 1 unit of BAP per ug of vector at 60° C. for about 1 hr. In order to recover the nucleic acid fragments, the preparation is extracted with phenol/chloroform and ethanol precipitated and desalted by application to a Sephadex ® G-50 spin column. Alternatively, religation can be prevented in vectors which have been double digested by additional restriction enzyme digestion of the unwanted fragments.

For portions of vectors derived from cDNA or genomic DNA which require sequence modifications, site specific primer directed mutagenesis may be used. This is conducted using a synthetic oligonucleotide primer complementary to a single-stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having the mutated form as a single strand; 50% will have the original sequence. The resulting plaques are hybridized with kinased synthetic primer under allele-specific conditions. In general, one may vary the temperature, ionic strength, and concentration of chaotropic agent(s) in the hybridization solution to obtain conditions under which substantially no probes will hybridize in the absence of an "exact match." For hybridization of probes to bound DNA, the empirical formula for calculating optimum temperature under standard conditions (0.9M NaCl) is $$T(°C.) = 4(N_G + N_C) + 2(N_A + N_T) - 5° C.,$$

where $N_G$, $N_C$, $N_A$, and $N_T$ are the numbers of G, C, A, and T bases in the probe (J. Meinkoth et al, *Anal Biochem* (1984) 138:267-84).

Plaques which hybridize with the probe are then picked, cultured, and the DNA recovered.

One may express polypeptides in vitro, and incorporate "non-natural" amino acids using the technique disclosed by C. J. Noren et al, *Science* (1989) 244:182-88. Briefly, an in vitro expression vector is prepared, and the codon position corresponding to the non-natural amino acid site is altered to a nonsense codon (particularly TAG), e.g., using oligonucleotide-directed mutagenesis. A corresponding tRNA is prepared and acylated in vitro with the desired non-natural amino acid (e.g., 4-fluorophenylalanine, phenylglycine, and the like). Expression of the altered vector in a cell-free system in the presence of the acylated tRNA provides the polypeptide incorporating the non-natural amino acid.

Verification of Construction

Correct ligations for plasmid construction may be confirmed by first transforming *E. coli* strain MM294 obtained from *E. coli* Genetic Stock Center, CGSC #6135, or other suitable host with the ligation mixture. Successful transformants are selected by ampicillin, tetracycline or other antibiotic resistance or using other markers depending on the plasmid construction, as is understood in the art. Plasmids from the transformants are then prepared according to the method of D. B. Clewell et al, *Proc Nat Acad Sci USA* (1969) 62:1159, optionally following chloramphenicol amplification (D. B. Clewell, *J Bacteriol* (1972) 110:667). The isolated DNA is analyzed by restriction and/or sequenced by the dideoxy method of F. Sanger et al, *Proc Nat Acad Sci USA* (1977) 74:5463 as further described by Messing et al, *Nuc Acids Res* (1981) 9:309, or by the method of Maxam et al, *Meth Enzymol* (1980) 65:499.

Antibodies

Anti-DARP antibodies, both polyclonal and monoclonal, may be prepared by conventional methods. In general, purified DARP (as described above) is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the DARP in saline, preferably in an adjuvant such as Freund's complete adjuvant, and injecting the mixture or emulsion parenterally (generally subcutaneously or intramuscularly). A dose of 50-200 ug/injection is typically sufficient. Immunization is generally boosted 2-6 weeks later with one or more injections of DARP in saline, preferably using Freund's incomplete adjuvant. One may alternatively generate antibodies by in vitro immunization using methods known in the art, which for the purposes of this invention is considered equivalent to in vivo immunization.

Polyclonal antisera is obtained by bleeding the immunized animal into a glass or plastic container, incubating the blood at 25° C. for one hour, followed by incubating at 4° C. for 2-18 hours. The serum is recovered by centrifugation (e.g., 1,000× G for 10 minutes). About 20-50 mL per bleed may be obtained from rabbits.

Monoclonal antibodies are prepared using the method of Kohler and Milstein, *Nature* (1975) 256:495-96, or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of non-specifically adherent cells) by applying a cell suspension to a plate or well coated with DARP. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected MAb-secreting hybridomas are then cultured either in vitro (e.g., in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}I$ may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with $^{125}$I, or with an anti-biotin MAb labeled with HRP. Other permutations and possibilities will be readily apparent to those of ordinary skill in the art, and are considered as equivalents within the scope of the instant invention.

One may also prepare Ab derivatives, for example Fab and F(ab')$_2$ fragments, chimeric antibodies, and the like. Such derivatives, particularly fragments lacking the Fc antibody region, may be preferred in therapeutic applications.

Antibodies of the invention may be assayed for binding avidity and neutralizing activity by standard methods. Measurement of neutralizing activity is conveniently accomplished by adding a known quantity of antibody to a rat brain tissue section in the presence of DARP and determining the inhibition of dopamine-releasing activity.

Anti-DARP antibodies are useful in immunometric assays for determining the concentration of DARP, either for determinations of DARP purity and activity as an adjunct to production, or for diagnosis of pathological conditions due to over- or under-abundance of DARP. Neutralizing anti-DARP antibodies are further useful therapeutically for counteracting the effects of over-expression of dopamine or DARP, for example hyperactivity and schizophrenic behavior.

Use and Administration

DARP can potentially be used to treat disorders characterized by an under-abundance or lack of dopamine, particularly Parkinson's disease. DARP may also be useful for inhibiting secretion of prolactin by releasing endogenous dopamine from the tuberoinfundibular region (for example in pituitary prolactinomas).

DARP is administered to the central nervous system by injection into the cerebrospinal fluid (CSF), by cannula directly to cerebral ventricles, by controlled-release implant positioned within the ventricles or directly into specific areas of the brain, and the like. Due to the high natural abundance of DARP within the adrenal glands, it is possible that DARP may be capable of crossing or being transported across the blood-brain barrier. Accordingly, it is believed that administration by intravenous and intramuscular injection will also be effective. DARP is preferably administered in the form of an aqueous solution or suspension, e.g., using Ringer's solution, phosphate-buffered saline, or the like. Other agents may be added to stabilize and preserve the formulation, for example, lactose, EDTA, antibiotics, citrate, ascorbate, human serum albumin, and the like. DARP may be formulated either in liquid form, or as a lyophilized powder or cake for reconstitution prior to administration. A detailed discussion of suitable pharmaceutical excipients and liquid carriers may be found in E. W. Martin, "Remington's Pharmaceutical Sciences" (Mack Pub. Co.).

The effective amount of DARP refers to the amount necessary to achieve the desired release of dopamine. The precise amount required will vary depending upon the particular disorder to be treated, the age of the subject, the severity of the subject's condition, the route of administration, and so forth, but may be determined by routine experimentation. In general, however, an effective concentration within the substantia nigra will range from about $10^{-11}$ to $10^{-8}$M (about 0.01 to about 10 nM). This concentration may be achieved by administration directly to the cerebral ventricles, or by administering a somewhat larger amount intravenously. Inhibition of prolactin secretion by pituitary tumors may require higher or lower amounts, but the amount may be titrated in the patient by administering DARP followed by assaying the patient's serum for prolactin concentration.

Anti-DARP antibody (Ab) must generally be administered directly to the cerebral ventricles if it is to have a therapeutic effect: Abs are not expected to cross the blood-brain barrier. It may be preferable to use Abs or Ab derivatives which do not fix complement, in order to minimize the potential for tissue damage. Abs are administered in the form of an aqueous solution or suspension, e.g., as described above for DARP. The anti-DARP Abs may be formulated either in liquid form, or as a lyophilized powder or cake for reconstitution prior to administration. A detailed discussion of suitable pharmaceutical excipients and liquid carriers may be found in "Remington's Pharmaceutical Sciences."

The effective amount of anti-DARP Abs refers to the amount necessary to achieve the desired inhibition of dopamine release by DARP. The precise amount required will vary depending upon the Ab avidity, the particular disorder to be treated, the age of the subject, the severity of the subject's condition, the route of administration, and so forth, but may be determined by routine experimentation.

DARP activity may be determined by means of a dopamine release assay, for example as described for MPTP by Chang and Ramirez, *Brain Res* (1986) 368:134–40. Briefly, male rats are decapitated, and the striatal tissue dissected from the brain and placed in a chamber superfused with Krebs-Ringer phosphate buffer (KRP). The tissues are allowed to stabilize for about 40 minutes. Perfusate samples are collected on ice for nine 20 20 minute intervals, at a flow rate of about 30–35 uL/min. At the beginning of the fourth collection period, KRP containing a test quantity of DARP is infused for 40 minutes. The perfusate samples are analyzed for dopamine, 3,4-dihydroxyphenylacetic acid, epinephrine, 5-hydroxyindoleacetic acid, homovanillic acid, and norepinephrine in 20 uL aliquots by HPLC, using electrochemical detection.

DARP activity may also be assayed in vivo using a technique we have developed. A "push-pull" cannula 1 is prepared as illustrated in FIG. 1A. A 24 gauge cannula 2 is fitted concentrically with a 33 gauge cannula 3, defining an inner lumen within cannula 3, and an outer lumen defined by the space between cannula 3 and cannula 2. This assembly is provided with a body 5, a collar 6, a base 9 for attachment to the skull of the subject, and means 8 for firmly affixing said base to the skull. The body 5 is further provided with a 29 gauge cannula 4 which provides an exit for fluid drawn through the outer lumen of cannula 2. Body 5 and collar 6 define a void 10 which receives the fluid drawn up through said outer lumen, which then passes into cannula 4. The region between the base 9 and collar 6 is preferably filled with a physiologically acceptable polymer 7 to increase the rigidity of the assembly. It is preferred to construct the device of materials which will not cause undue inflammation following implantation, and which will not significantly absorb the compounds administered or extracted through the cannula. The dimensions of this device described are appropriate for use in rats: the device may be altered as appropriate for other subjects, such as sheep, rabbits, and monkeys. We have found that a cannula length of about 8.2 mm is appropriate for cannula 2.

The device of FIG. 1A is surgically implanted in the subject's brain, positioned so that the cannula tip delivers the test compound to the caudate nucleus. It is preferred to prepare a channel for the cannula by first inserting a stylette as depicted in FIG. 1B, having a probe of about 34 gauge coated with clear nail polish (opulence base 18 coat) to minimize tissue damage and irritation. The stylette is removed, and the cannula assembly inserted, with attachment means 8 used to affix the device to the subject's skull. The attachment means may include cement, bone screws, and the like. The scalp is closed and sutured around the polymer portion 7 of the base of the device. The subjects are caged individually, and are allowed to recover and adapt to the device for a period of 10–15 days. The device allows nearly unrestricted motion for the subject.

In operation, DARP (or other test compounds) is supplied in an aqueous solution, and is conducted to cannula 3 by suitable means, for example a peristaltic pump. A flow rate of about 12 uL/min is generally suitable. Cannula 4 is connected to another pump (preferably a peristaltic pump) adjusted to withdraw solution at the same rate as the first pump administers solution. The samples are pooled and analyzed by HPLC.

C. EXAMPLES

The examples presented below are provided as a further guide to the practitioner of ordinary skill in the art, and are not to be construed as limiting the invention in any way.

EXAMPLE 1

Preparation of DARP (A) Preparation from Fresh Tissue

Fresh tissues of whole adrenal glands, neocortex, corpus striatum, and cerebellum from male and female rats were sonicated in a solution of 40% EtOH/6% ammonium acetate, pH 5.1. Following centrifugation at 5000 g for 30 min, the EtOH concentration of the supernatant is brought up to 80%. After storage at $-20°$ C. overnight, the precipitate is collected by centrifugation at 5000 g for 30 min. The 80% EtOH precipitate is then dissolved, dialyzed against a modified Krebs-Ringer phosphate buffer.

Preparation from Dried Extracts

Bovine adrenal cortex acetone powder (50 g, Sigma product A3141) was extracted with 400 mL of 40% EtOH/6% ammonium acetate (pH 5.1) containing 0.12 mg/mL of phenylmethylsulfonyl fluoride (PMSF). Extraction was conducted overnight with stirring, at 0°–4° C. The resulting mixture was centrifuged at 15,000 g for 30 min and the supernatant retained. The residue was extracted again for 90 min at 0°–4° C. using 400 mL of EtOH/acetate/PMSF solution. After centrifugation, the supernatants were combined (Fraction I).

The EtOH concentration of Fraction I was slowly raised to 80% by adding ethanol precooled to $-20°$ C. The mixture was allowed to stand at $-20°$ C. for 18 hours. The upper 75% of the mixture was siphoned off, and the precipitate collected by centrifugation at 15,000 g at $-20°$ C. for 20 min. The precipitate was dissolved in 0.5M ammonium bicarbonate, centrifuged for 15 min at 8,000 rpm to remove undissolved materials, and brought to a final volume of 20 mL with 0.5M ammonium bicarbonate (Fraction II).

Fraction II was applied to a Sephadex ® G-100 column (4.6×90 cm) equilibrated with 30 mM ammonium bicarbonate. Elution was performed at 0°–4° C. with 30 mM $NH_4HCO_3$ and 6 mL fractions collected. DARP activity appeared in the elution volume corresponding to a molecular weight range between 41 and 51 kDa (Fraction III).

Fraction III was fractionated at 0°–4° C. by the slow addition of a solution containing 0.1M $ZnCl_2$ in 5 mM HCl (pH 3.0), to a final $ZnCl_2$ concentration of 32 mM. The pH of the final mixture was 5.1. After equilibration for 10 min at 0°–4° C., the precipitate was removed by centrifugation. To the supernatant (about 100 mL) was added 1/10 volume of 1M EDTA, and the sample dialyzed overnight against 2 L of 30 mM $NH_4HCO_3$ at 0°–4° C. (Fraction IV).

Fraction IV was applied to a DEAE-Sephadex ® A-25 column (1×11 cm) at room temperature, equilibrated in 30 mM $NH_4HCO_3$. After application of the sample, the column was washed with 3 column volumes of 30 mM $NH_4HCO_3$. The absorbance of the effluent at 280 nm decreased to nearly 0. Elution of DARP was then performed formed with 150 mM $NH_4HCO_3$. Fractions of 1 mL were collected and pooled based on absorbance at 280 nm (Fraction V).

EXAMPLE 2

Characterization of DARP (A) Gel Electrophoresis

Figure 2:
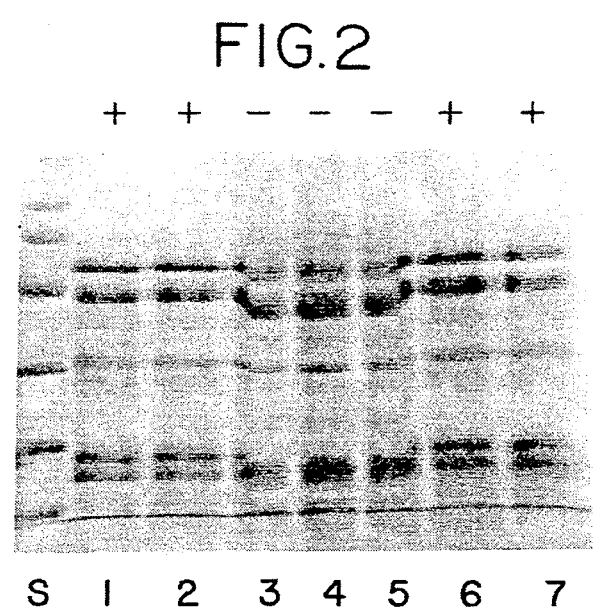
FIG. 2 is the SDS-PAGE pattern of DARP. The figure shows the Coomassie blue stained gel of purified DARP electrophoresed with [(+); lanes 1, 2, 6 and 7] and without [(−); lanes 3, 4, and 5] the addition of 40 mM dithiothreitol to the samples. Lane S shows the molecular weight standards phosphorylase b (97 kDa), bovine serum albumin (68 kDa), ovalbumin (43 kDa), carbonic anhydrase (29 kDa), and soybean trypsin inhibitor (21.5 kDa).

Polyacrylamide (12.5%) gel electrophoresis of purified DARP was performed in the presence of sodium dodecyl sulfate (SDS) essentially as described by Laemmli, *Nature* (1970) 227:680. Prior to electrophoresis, samples were heated for 2.5 min at 90° C. either in the presence of absence of 40 mM dithiothreitol (DTT). The results are depicted in FIG. 2. Lanes 1, 2, 6, and 7 are those in which the sample was reduced with DTT, and indicates that purified DARP exhibits 5 major electrophoretic bands. Their subunit molecular weights are about 49, 42, 32, 20, and 18 kDa, as determined in comparison with known molecular weight standards (lane S).

The samples in lanes 3, 4 and 5 were not reduced with DTT, to allow detection of disulfide bonding (R. J. Allore et al, *Anal Biochem* (1984) 137:523). The results indicate that the major bands (except the 20 kDa band) contain intramolecular disulfide bonds.

(B) Molecular Weight Determination

The native (non-denatured) molecular weight of DARP was determined by the technique of Andrews, *Biochem J* (1965) 96:595, using gel filtration on a Sephadex ® G-100 column. The column was calibrated with a mixture containing bovine serum albumin (Mr 68,000), chicken egg albumin (Mr 43,000), and bovine erythrocyte carbonic anhydrase (Mr 29,000). The molecular weight of DARP was determined to be 46,000±5,000.

(C) Protease Sensitivity

DARP (50 uL) was treated with trypsin in 30 mM $NH_4HCO_3$ at a 10:1 ratio of DARP to trypsin. After incubation for 16 h at 22° C., the reaction was halted by adding 10 ug of soybean trypsin inhibitor (Sigma product T9003). This treatment reduced DARP activity by about 90%.

(D) Thermolability

DARP (30 ug) was heated for 60 min at 100° C. in 30 mM NH$_4$HCO$_3$. This treatment completely eliminated DARP activity.

EXAMPLE 3

Demonstration of Activity (A) In vitro Perfusion

Adult male Sprague-Dawley rats weighing 300–500 g were housed in animal quarters at a temperature of 23° C. on a light-dark cycle of 14 h light:10 h dark, with lights on at 05:00 h. Water and Purina rat chow were available ad libitum. All rats were allowed 7 days to become accustomed to the environment prior to experiment.

Figure 3:
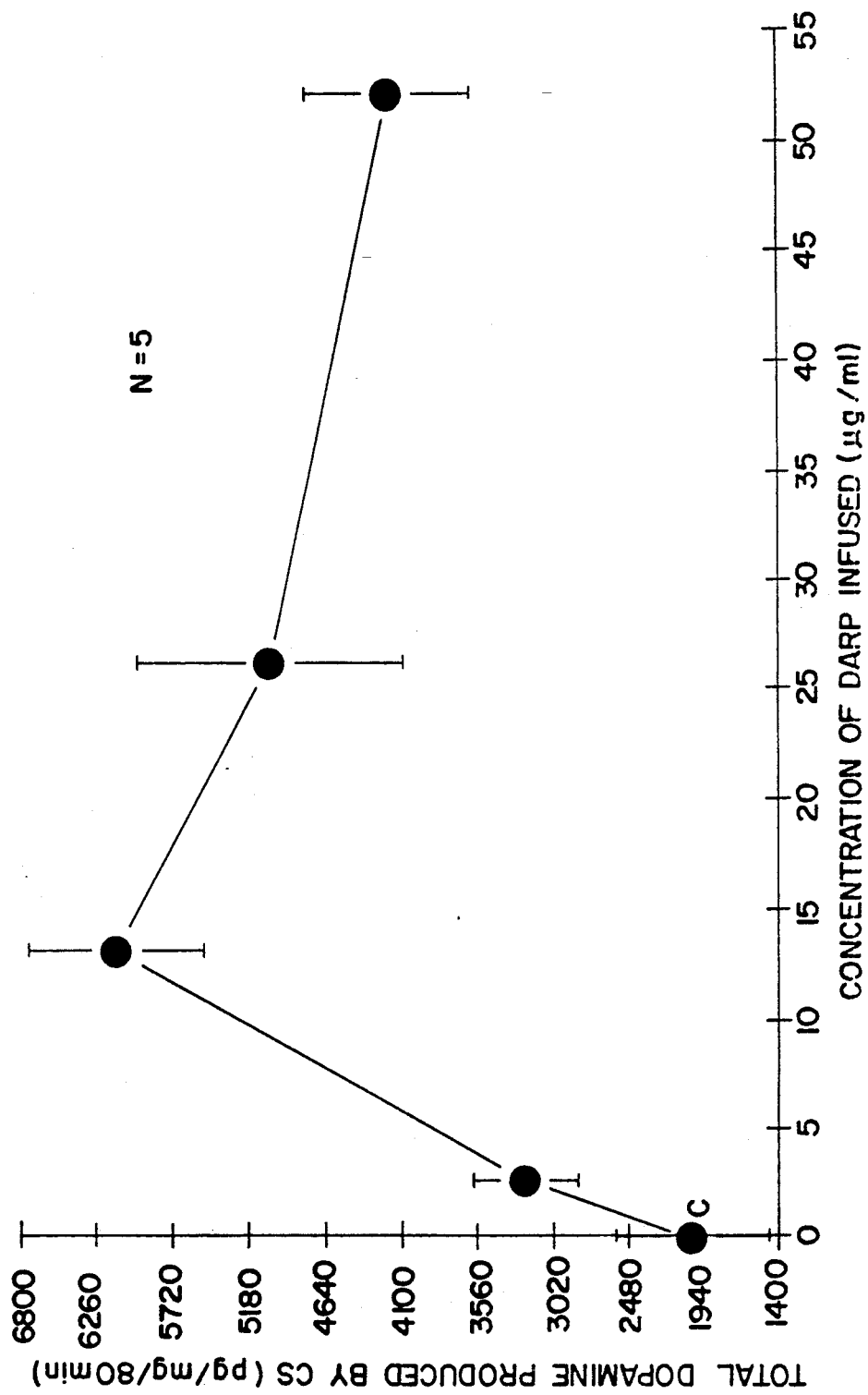
FIG. 3 graphically depicts the results of the in vitro superfusion experiment described in Example 3A. The graph shows the results of superfusion 0–52 ug/mL DARP into dissected rat corpus striatal tissue, depicting dopamine produced in pg/mg tissue over 80 minutes versus DARP in ug/mL.

Animals were killed by decapitation between 10:00 and 14:00 h. The corpus striatum was dissected out and placed in ice-chilled Krebs-Ringer phosphate medium, pH 7.4, containing 0.18% glucose (KRP). Striatal tissue from both sides of the brain of one animal was used in each superfusion chamber. The superfusion system was a miniaturized version of the device described in Gallardo and Ramirez, *Proc Soc Exp Biol Med* (1977) 155:79–84. Each superfusion chamber was positioned in a constant temperature bath maintained at 37° C. The median volume in the chamber (about 100 uL) was replaced at a constant flow rate of 25 uL/min. The striatal tissue fragments were placed in the chamber and allowed to stabilize for 30 min. The chambers were then superfused with KRP containing from 0 to 52 ug/mL DARP. Effluent samples were then collected on ice at 10 min intervals for 80 minutes. After 80 min of perfusion, the tissue is removed from the superfusion chamber and immediately assayed for dopamine content. The total dopamine produced per mg is calculated as the total amount of dopamine collected during superfusion plus the amount determined in the tissue at the end of the experiment, divided by the tissue weight at the end of the experiment. The results (mean ± standard error, N=5) are shown in FIG. 3, with dopamine produced in pg/mg tissue versus DARP in ug/mL. The maximal response occurred at 13 ug/mL.

(B) In vivo Perfusion

A push-pull cannula as depicted in FIG. 1A was implanted in the caudate nucleus of a male rat, and the animal allowed to recover for 10 days. Following the recovery period, the rat was perfused with KRP medium at a flow rate of 12 uL/min. The perfusate was collected and pooled in 10 min fractions. At intervals 6 and 10, DARP was infused for 20 min at a concentration of 10 ug/mL. Each fraction was immediately assayed for dopamine concentration.

Figure 4:
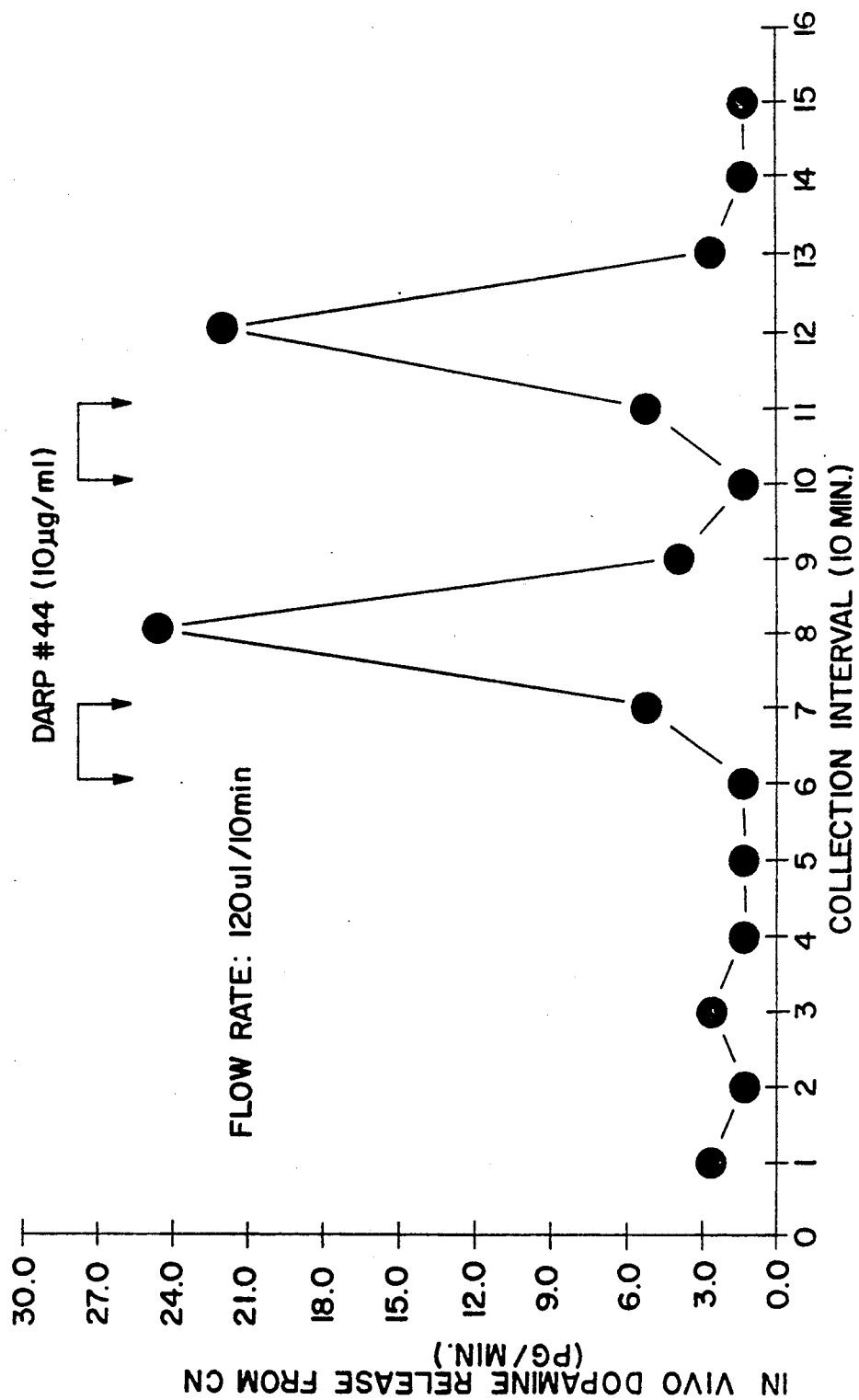
FIG. 4 graphically depicts the results of the in vivo perfusion experiment described in Example 3B. The graph shows the concentration of dopamine released in pg/min as a function of collection fraction number, with 10 ug/mL DARP infused for 20 min at the beginning of fractions 6 and 10.

The results are depicted in FIG. 4, as dopamine release rate in pg/min versus collection fraction. The data shows a rapid and marked rise in DA release rate, from a baseline concentration of about 1.0 pg/min to a peak of about 23–25 pg/min. Both pulses of DARP were accompanied by a burst of amphetamine-like stereotype behaviors, such as intense locomotion around the cage, repetitive rearing, sniffing, head-bowing, and in some cases front paw tremors. The behavioral effects subsided within 30–40 min following DARP infusion.

EXAMPLE 4

Preparation of Anti-DARP Antibodies (A) Preparation: Fraction V DARP (50 ug, emulsified in Freund's complete adjuvant) was administered to adult mice on day 1. On days 21 and 42, additional doses of Fraction V DARP (50 ug) were administered emulsified in Freund's incomplete adjuvant. Serum was assayed periodically for presence of anti-DARP antibodies. Once anti-DARP Abs were found, the spleens were then removed from the responding animals and dissociated into single cells. Nonadherent cells were collected and applied to a microtiter plate having bound DARP. Cells failing to adhere to the DARP plate were rinsed away, and adherent cells were fused with Sp20-Ag14 mouse myeloma cells essentially following the method of Kohler and Milstein, *Nature* (1975) 256:495–96. The resulting hybridomas were cloned by limiting dilution, and selected for immunoreactivity with Fraction V DARP. Selected hybridomas were propagated as ascites tumors.

(B) Activity of Anti-DARP MAbs: The in vitro superfusion experiment described in Example 3(A) above was repeated with the following variations.

Tissue in group A was superfused with KRP at a flow rate of 23 uL/min, with perfusate fractions collected every 10 min. At the beginning of fraction 3, the tissue was superfused with 1.3 ug DARP in 500 uL KRP.

Tissue in group B was superfused with KRP at a flow rate of 25 uL/min, with perfusate fractions collected every 10 min. At the beginning of fraction 3, the tissue was superfused with 50 uL of ascites fluid from the E$_2$-3-F$_3$ hybridoma prepared in part (A) above.

Tissue in group C was superfused with KRP at a flow rate of 35 uL/min, with perfusate fractions collected every 10 min. Ascites fluid from the E$_2$-3-F$_3$ hybridoma (50 uL) was incubated with DARP (1.3 ug in 50 uL KRP) at room temperature for 1.5 hr, then resuspended in 500 uL KRP. At the beginning of fraction 3, the tissue was superfused with the DARP/MAb suspension.

Tissue in group D was superfused with KRP at a flow rate of 35 uL/min, with perfusate fractions collected every 10 min. Boiled ascites fluid from the E$_2$-3-F$_3$ hybridoma (50 uL) was incubated with DARP (1.3 ug in 50 uL KRP) at room temperature for 1.5 hr, then resuspended in 500 uL KRP. At the beginning of fraction 3, the tissue was superfused with the DARP/boiled MAb suspension.

The results are shown in FIG. 5. FIG. 5A shows that administration of DARP alone raised dopamine concentration from a baseline of about 10 pg/mg/min to a peak of about 158 pg/mg/min. FIG. 5B shows that administration of MAbs alone had no effect on the baseline DA release. FIG. 5C shows that MAbs obtained from E$_2$-3-F$_3$ hybridoma completely neutralized DARP activity. FIG. 5D shows that the boiled MAbs are substantially less able to neutralize DARP activity.

What is claimed:

1. Dopamine releasing protein, substantially free of other adrenal proteins and brain-derived proteins, which is capable of selectively stimulating the dose-dependent release of dopamine from striatal tissue.

2. Dopamine releasing protein, in substantially pure form, which is capable of selectively stimulating the dose-dependent release of dopamine from striatal tissue.

3. A composition capable of inducing release of dopamine from dopaminergic neurons, which composition comprises:

an effective amount of dopamine releasing protein, wherein said dopamine releasing protein is capable of selectively stimulating the dose-dependent release of dopamine from striatal tissue; and a pharmaceutically acceptable excipient.

4. The composition of claim 3, wherein said dopamine releasing protein is present at a concentration of about 0.001 to about 10 nM.

5. An antibody which binds specifically to dopamine releasing protein, wherein said dopamine releasing protein is capable of selectively stimulating the dose-dependent release of dopamine from striatal tissue.

6. A composition for inhibiting the release of dopamine within a vertebrate nervous system, which composition comprises:

an effective amount of a neutralizing antibody or antibody derivative specific for dopamine releasing protein, wherein said dopamine releasing protein is capable of selectively stimulating the dose-dependent release of dopamine from striatal tissue; and a pharmaceutically acceptable excipient.

* * * * *